United States Patent

Ratzker et al.

[11] Patent Number: 5,316,650
[45] Date of Patent: May 31, 1994

[54] ELECTROFORMING OF METALLIC GLASSES FOR DENTAL APPLICATIONS

[76] Inventors: Menahem Ratzker, 1131 University Blvd., West Silver Spring, Md. 20902; David S. Lashmore, 5506 Woodlyn Rd., Frederick, Md. 21701; John A. Tesk, 13446 Pond Filed Ct., Highland, Md. 20777

[21] Appl. No.: 19,489

[22] Filed: Feb. 19, 1993

[51] Int. Cl.$^5$ .............................................. C25D 1/10
[52] U.S. Cl. ..................................... 205/67; 205/258
[58] Field of Search .................................. 205/67, 258

[56] References Cited

U.S. PATENT DOCUMENTS

| | | | |
|---|---|---|---|
| 1,612,605 | 12/1926 | Buenaventura | 205/70 |
| 2,200,743 | 5/1940 | Hardy | 148/240 |
| 2,643,221 | 6/1953 | Brenner et al. | 205/258 |
| 3,152,974 | 10/1964 | Zentner | 205/103 |
| 3,578,571 | 5/1971 | McQuaid et al. | 205/258 |
| 3,857,683 | 12/1974 | Castonguay | 205/152 |
| 3,986,901 | 10/1976 | Plante et al. | 248/105 |
| 4,451,236 | 5/1984 | Tarasov et al. | 433/207 |
| 4,594,104 | 6/1986 | Reybould | 75/243 |
| 4,673,468 | 6/1987 | Myers et al. | 205/101 |
| 4,756,747 | 7/1988 | Haushalter | 75/370 |
| 4,874,577 | 10/1989 | Wakita et al. | 420/417 |
| 4,891,183 | 1/1990 | Corwin | 420/435 |
| 5,088,923 | 2/1992 | Andreiko | 433/9 |

Primary Examiner—T. M. Tufariello
Attorney, Agent, or Firm—Millen, White, Zelano & Branigan

[57] ABSTRACT

In a process of electroforming a metal to produce a dental prosthesis, the improvement comprising employing as the metal a metallic glass alloy such as cobalt and phosphorus containing 8–30% by weight of phosphorus. The electrolytic bath comprises:
15–300 g/L $CoSO_4.7H_2O$
40–80 g/L $CoCl_2.6H_2O$
25–35 g/L $H_3BC_3$
30–100 g/L $H_3PO_3$
1–2 ml/L wetting agent
pH about 0.8–2.0.

15 Claims, 3 Drawing Sheets

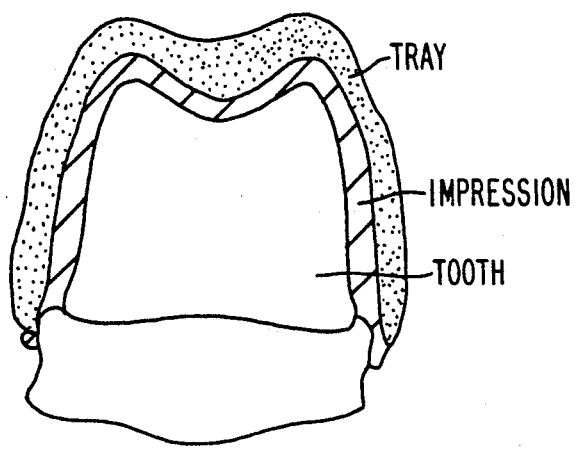
FIG. IA
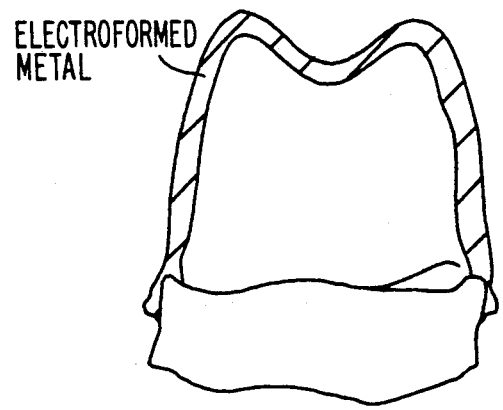
FIG. ID
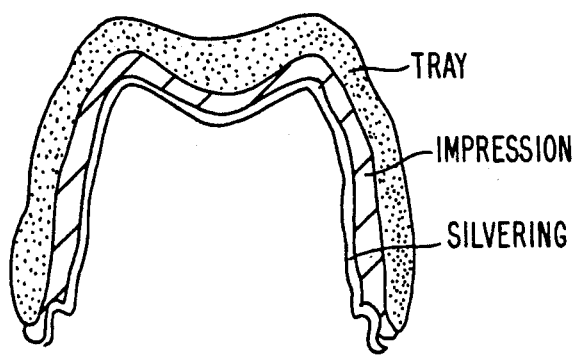
FIG. IB
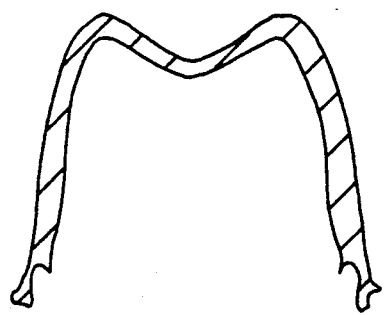
FIG. IE
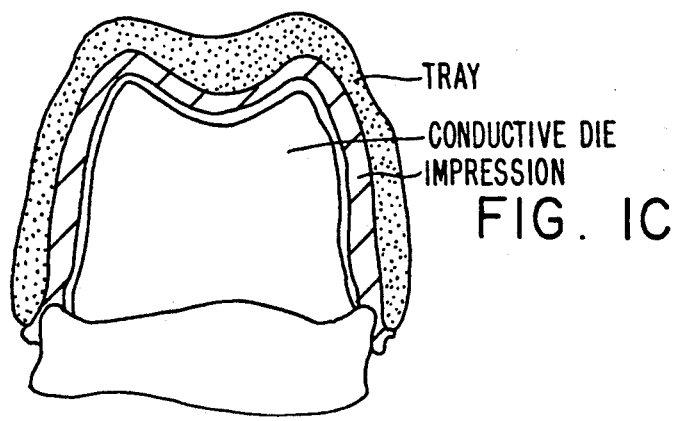
FIG. IC

ELECTROFORMING OF METALLIC GLASSES FOR DENTAL APPLICATIONS

FIELD OF THE INVENTION

This invention relates to a method of electroforming metallic glasses to produce dental prostheses, the electrolyte composition employed, and the resultant dental prostheses.

BACKGROUND OF THE INVENTION

The current casting methods for fabricating dental prostheses contain many steps where errors or inaccuracies can occur and accumulate. In general, an impression of the teeth surface and the adjacent areas is taken with an impression material that is typically a polymeric elastomer. This impression is then used for making a cast stone or plaster die. A wax model of a prosthesis is built on this die. The model is removed and invested in refractory material. Once the refractor has set, the wax is removed by heating to make the refractory mold. The metal is then cast into the mold. The accuracy of this process is greatly influenced by the materials used, the laboratory techniques, and the skill of the technicians. Errors incorporated in each stage can accumulate to cause misfit of the prosthesis. The strength, durability, and biocompatibility of the prosthesis are clearly determined by the available casting metals.

Electroforming as an alternative to casting in dentistry has been described by a number of investigators. Electroforming has the immediate advantage of being able to replicate surface features of less than 1 $\mu$m which, in general, will not be affected by subsequent processing. More than three decades ago, Rogers and Armstrong reported on a combined electroforming-casting method. Rogers et al., *J. Prost. Dent.*, 11: 959-960 (1961). They electroformed gold on a silver-painted die stone. After electroforming the matrix, gold was cast onto the matrix to form an inlay. Rogers later reported that the gold matrix was removed by heating the matrix and the die, followed by rapid cooling to disintegrate the die. Rogers, *Austr. Dent.*, 15: 316-323 (1970); U.S. Pat. No. 3,997,637 (Rogers). In subsequent years, Rogers reported on the gold electroforming casting technique. Rogers, *Austr. Dent. J.*, 21: 479-487 (1976); Rogers, *Austr. Dent. J.*, 22: 100-106 (1977); Rogers, *Austr. Dent. J.*, 4: 163-170 (1979); Rogers, *Austr. Dent. J.*, 25: 1-6 (1980); Rogers, *Austr. Dent. J.*, 25: 205-208 (1980). Tettammati et al. reported on crowns prepared by electrodeposition. Tettammati et al., *Rev. Circ. Argent. Odontol.*, 32-35 (1969).

In 1971, Wismann was granted U.S. Pat. No. 3,567,592 for an electroplated cermet alloy. In this patented process, a die stone coated with lacquer is metallized in a copper or silver solution. The die is then electroplated in a solution containing ceramic and metallic particles. A metal particularly well suited for this process is nickel. Later, Wismann in 1984 was granted U.S. Pat. No. 4,488,590 on electroforming of gold on dies made of a low-melting-temperature alloys that subsequently could be easily removed by moderate heating. The die was first electroplated with a thin layer of copper or nickel. After completion of the electroforming process, the die was removed by melting, and the nickel or copper substrate was chemically removed in an electrolyte that would not attack the gold.

Many reports were published on electroforming of dental prostheses: de Freitas, *Rev. Bras. Odontol.*, 30: 96-102 (1973); French Patent No. 2,316,356 (Serfaty, 1977); Sifaoui, *Rev. Fr. Prothese Dent.*, 62-68 (1980); J. P. Kokai 8355592 A2 (Mitsara, 1983); Vrijhoef et al., *Restorative Dentistry*, 1: 143-146 (1985); Renggli et al., *Dental-Labor* (Munch), 33: 1655-1657 (1985); and DE 38 09 435 A1 (Yamashita et al.). Hayashi, *Kanagawa Shigaku*, 20: 58-75 (1985), and Chung, *Kanagawa Shigaku*, 22: 32-49, report a metal plate denture electroformed of Ni-CO alloy. In Watanabe et al., *Kanagawa Shigaku*, 23: 622-628 are reported. Kober et al., *Zahnarztl Mitt.*, 77: 2406-2409. Klett et al. (1987), *Dtsch. Zahnarztl Z.*, 42: 614-617; Klaus, *Quintessenz Zahntech*, 14: 1229-1240 (1988); Menne, *Quintessenz Zahntech*, 15: 1057-1064 (1989); and Stroppe, *Dental-Labor* (Munch), 38: 201-202 (1990), report work concerning electroforming of metals for dental prostheses. However, all of the alloys studied—gold, nickel, or nickel-cobalt—are either not strong enough to be used in thin sections where substantial strength is needed, or they lack biocompatibility.

SUMMARY OF THE INVENTION

An object of this invention is to provide an improved method of electroforming metals to produce dental prostheses.

Another object is to provide electrolyte solution for the purposes of conducting the process.

Still another object is to provide improved metallic dental prostheses.

Upon further study of the specification and appended claims, further objects and advantages of this invention will become apparent to those skilled in the art.

To attain the objects of this invention, there is provided a process of electroforming metals for dental prostheses, wherein metallic glass alloys of cobalt and phosphorus are electrodeposited on a substrate. Although metallic glass alloys have been known for decades, it was neither known nor at all predictable whether a cobalt-phosphorus glass alloy would be satisfactory for dental prostheses in view of the particular mechanical and corrosion-resistance specifications for such prostheses.

In particular, it has been discovered that a cobalt-phosphorus metallic glass alloy having a composition of about 8-30%, preferably at least 10%, by weight of phosphorus are suitable. Small amounts, e.g., up to about 20 wt %, preferably 3-20 wt %, of chromium and/or molybdenum are optionally included in order to enhance the corrosion resistance of the product.

In order to produce the dental prostheses, a conventional method of electroforming is employed comprising:

(1) producing an impression of a patient's teeth;

(2) chemically depositing a layer of silver inside said impression;

(3) casting a conductive material, e.g., a silver-filled epoxy, inside the impression;

(4) coating the resultant die with lacquer in areas where electrodeposition is undesired;

(5) immersing the die in an electrolyte and passing a current through the electrolyte and the die for a sufficient time to obtain the desired thickness of the cobalt-phosphorus metallic glass alloy;

(6) optionally, grinding rough edges of the electroformed prosthesis; and (7) dissolving said die in a solvent, e.g., a mixture of methylene chloride and formic acid.

It is also desirable, prior to step (2), to sensitize the impression with a solution of stannous chloride, for example. As the conductive substrate, a wide variety of materials can be utilized, both metals and non-metals, e.g., copper, stainless steel, silver filled epoxy, and other plastics having a conductive surface. Conductive coatings can be produced, for example, by activation of the substrate and electroless or autocatalytic coating. Further details are found in the literature, e.g., Lowenheim, F. A., Electroplating, Fundamentals of Surface Finishing, McGraw-Hill, New York, 1978, 416–425. The substrate should also be able to withstand the temperature/time conditions in the electrolyte for obtaining the desired thickness.

It is also preferred, between steps (4) and (5), for the die to be immersed in a bright copper electrolyte, e.g., Udilyte, UBAC® acid copper, so that a copper layer of about 2 to 20, preferably about 20 $\mu$m, is formed on the die. The resultant copper layer is then dissolved in an acid solution after step (7) in order to leave room for an adhesive.

It is generally desired for the cobalt-phosphorus alloy to have a thickness of about at least 10, preferably 100–2000 $\mu$m, and especially at least about 500 $\mu$m.

For the electroforming step, it has been discovered that as aqueous electrolyte a bath of the following composition yields satisfactory results (L represents 1 liter of solution):

| General | Preferred (g/L) |
|---|---|
| 15–300 g/L $CoSo_4.7H_2O$ | 200 |
| 40–80 g/L $CoCl_2.6H_2O$ | 60 |
| 25–35 g/L $H_3BO_3$ | 30 |
| 30–100 g/L $H_3PO_3$ | 50 |
| 1–2 ml/L wetting agent | 1 ml/L |
| pH about 0.8–2.0 | 1.0 |
| temperature about 40–85° C. | 75° C. |

The reason why the cobalt is added in the form of both the sulfate and chloride salts is that it is believed the sulfate improves ductility and the chloride improves anode dissolution.

If alloys containing chromium and/or molybdenum are desired, the above chemistry can be modified by the addition of chromium chloride ($CrCl_3.6H_2O$) 0.5 to 50 g/L or sodium molybdate ($Na_2MoO_4.2H_2O$) 5 to 50 g/L, with suitable complexing and buffering agents.

The function of the phosphorous acid is to provide a source of phosphorus and to act as a buffer whereas the boric acid functions to promote an improved charge transfer at the cathode.

When chromium is added and employed with appropriate complexing agents such as, for example, citrate, sulfonate, formic acid, pyrophosphate, ammonia, and thiocyanate, an alloy of Co-Cr can be obtained. The amount of Cr is 50 to 150 times the amount of Co. A ternary alloy of Co-Cr-Mo can be obtained by adding alkali metal molybdates to the cobalt solution.

Examples of alkali metal molybdates are $Na_2MoO_4.2H_2O$ and $K_2MoO_4.2H_2O$.

The function of the wetting agent is mainly to desorb hydrogen bubbles on the cathode surface. Any conventional ionic or non-ionic surfactant can be employed as the wetting agent, if suitable for use at temperatures up to 100° C. in acidic electrolytes. A host of wetting agents satisfy this requirement and compliance by an individual wetting can be determined by routine experimentation.

The electroforming step is conducted at about 40°–85° C., preferably 75° C., and it is also preferred that an inert gas, such as nitrogen, for example, is purged through the bath at a rate of about 1–10 cc/minute. The current may be direct current, preferably applied at between 150–300 mA/cm² or, alternatively, a pulsed galvanostatic current, preferably at about 300 mA/cm², preferably 200 $\mu$s on and 400 $\mu$s off. Deposition rate can be improved by ultrasonic agitation, rotation or fast stirring of the solution.

After the electroforming step, the die is dissolved, preferably in a solution of methylene chloride and formic acid, e.g., 90–95% methylene chloride and 5–10% formic acid.

BRIEF DESCRIPTION OF THE DRAWINGS

Various other objects, features and attendant advantages of the present invention will be more fully appreciated as the same becomes better understood when considered in conjunction with the accompanying drawings, and wherein:

FIGS. 1A, 1B, 1C, 1D, and 1E depict the steps employed in order to produce the cobalt-phosphorus electroformed dental prosthesis of the invention.

DETAILED DESCRIPTION OF FIGS. 1A, 1B, 1C, 1D, AND 1E

Figure 2:
FIG. 2 is a photograph of an electroformed dental prosthesis produced by the invention.

FIG. 1A shows the first step of taking an impression of a tooth. FIG. 1B shows the step of silvering the impression. FIG. 1C shows the step of casting a conductive die in the silvered impression. FIG. 1D shows the step of obtaining an electroformed metal on the surface of the conductive die. The conductive die is then removed from the impression, and metal is electroformed thereon, as shown in FIG. 1D. After the electroforming step on the die, the die is then dissolved in order to obtain a freestanding electroform, as shown in FIG. 1E. Thus, FIGS. 1A–1E provide, in effect, a somewhat abbreviated flowsheet, as compared to the description of the steps set forth in the "Summary of the Invention".

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited herein, are hereby incorporated by reference.

EXAMPLES

The electrolyte employed and the deposition parameters are presented in Table 1. The properties of the Co-P alloy are related to the phosphorus content.

Various samples were electroformed by use of several substrate geometries and mass transport conditions. Flat samples were also fabricated under uniform current density and uniform mass transport for the corrosion, microindentation hardness, and structural studies; and, finally, ring samples were fabricated on a rotating ring electrode, which allows mass transport to be controlled. The ring samples were subsequently used to measure the tensile strength of the metallic glass.

TABLE 1

| Composition and Deposition Parameters of the Electrolyte | |
| --- | --- |
| $CoSO_4.7H_2O$ | 200 g/L |
| $CoCl_2.6H_2O$ | 60 g/L |
| $H_3BO_3$ | 30 g/L |
| $H_3PO_3$ | 50 g/L |
| Wetting agent (such as Niaproof ® 08) | 1 ml/L |
| Temperature = 75° C. | |
| Current Density = 150 to 300 mA/cm$^2$ | |

Electroforming

Polymeric impressions used in this study were made by the usual dental clinical techniques. A polyether elastomer (Impregnum ®) was selected as the impression material because of its wetting ability and its smooth surface. The impression was metallized by a commercially available silvering process (London Laboratories Ltd.): The impression was first sensitized by a stannous chloride solution (Lon Lab ® BOL), and then it was immersed in a silver solution containing a reducing agent. Into certain types of impressions a silver solution was poured. A thin layer of silver metal was chemically deposited on the sensitized areas. The next step was to cast a die inside the metallized impression. This die was made of a conductive silver-filled epoxy resin The silver epoxy chosen for this study (Bipax ® TraDuct FS281) performed well in terms in viscosity, shrinkage, and porosity caused by bubbles. A linear change of 0.28% was measured on a die made of this silver-filled epoxy. Surfaces not to be electroformed were coated with a stop-off lacquer.

The cobalt-phosphorus metallic glass alloy was then electroformed until the desired thickness was obtained with the electrolyte described in Table 1. The processing sequence is summarized in FIG. 1. After the electroforming process, the edges of the electroformed alloy were ground to remove excess metal. The die was then dissolved in a solvent, leaving a free-standing electroformed structure with an inner surface that very accurately matched the surface of the tooth. An example of an electroformed dental prosthesis is shown in FIG. 2. For an actual prostheses, in order to make space for the restorative adhesive, a 20 μm-thick copper layer can be electroformed, on the die, prior to the Co-P layer. This copper layer can be dissolved in an acid solution, leaving a space of uniform thickness.

Microindentation Hardness

Microindentation hardness was measured on the cross section of three samples with the use of a Knoop Indentor. Hardness was measured as a function of load, which ranged from 10 g to 1000 g. At 100 g load, the as deposited hardness for one sample was 640 Knoop Hardness Number (KHN) and 1100 KHN, following heat treatment at 350° C. for one hour. Two other samples were measured at 100 g load, and the as-deposited hardness was 614 and 620 KHN. Microindentations were measured with the instrument optical system at a magnification of 400. The objective numerical aperture was 0.65. The estimated yield strength calculated from this hardness data, as suggested by Tabor (1951), is 1900 MPa for the as-deposited 88.2% Co-11.8% P alloy.

This yield strength is very high, and it allows fabrication of thin and wear-resistant structures from this material.

Corrosion Performance

In order to obtain information on how the Co-P alloys would behave in the mouth, several samples were subjected to accelerated corrosion tests in Hanks' solution (Hanks and Wallace, 1949). The only test performed was a simple potentiodynamic scan of the alloys themselves. These were not electrochemically coupled to other metals likely to be in the mouth such as silver amalgams or gold. No attempts were made to optimize the corrosion behavior by alloying. For these measurements, the surface roughness was not controlled. The samples were studied as deposited and were degreased in a series of solvents prior to immersion in the solution. To obtain a comparison with currently used dental alloys, cast Vitalliua ® alloy disks were polished with 4000 grit silicon carbide paper. These were then potentiodynamically scanned at the same rate in the same solution. A fresh solution was used for each experiment The corrosion potential was 200 mV to 300 mV vs. Saturated Calomel Electrode (SCE) for as-deposited Co-P samples and −100 mV to −120 mV vs. SCE for polished Vitallium ® samples. The average corrosion rate (5 samples ) was 0.8 mpy for Co-P alloys and 2.3 mpy for the Vitallium ® cast alloy.

Scanning Electron Microscopy (SEM)

Figure 3:
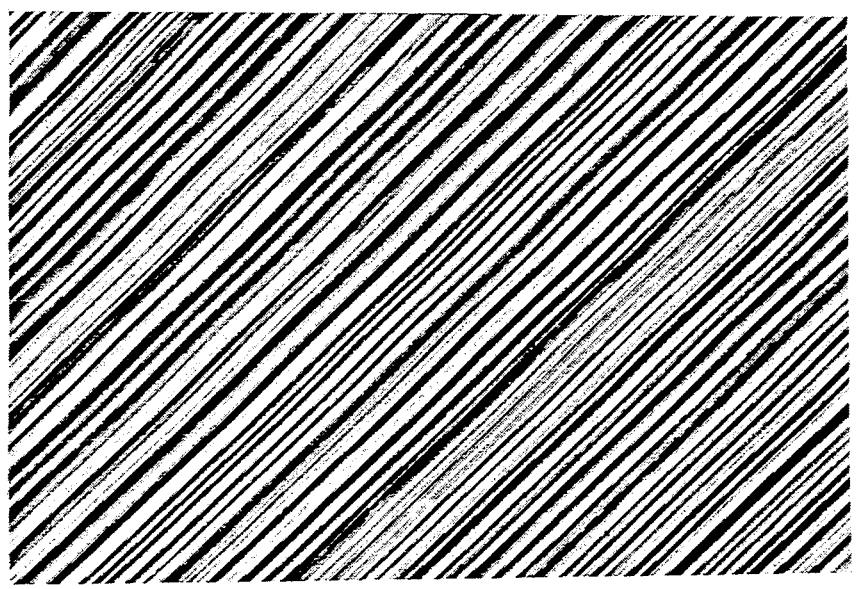
FIG. 3 is an electron microscope micrograph of the resultant electroformed Co-p alloy.

Scanning electron microscopy was used to analyze the samples for composition and surface morphology. Phosphorus contents varied from 8–15% by weight as a function of the deposition parameters. Some samples were also polished to 0.25 μm diamond, etched, and studied. A layered or banded structure was revealed in the etched samples, as shown in FIG. 3. This banded structure can be controlled by the deposition parameters, or even eliminated by them.

The preceding examples can be repeated with similar success by substituting the generically or specifically described reactants and/or operating conditions of this invention for those used in the preceding examples Moreover, the invention has many applications, including but not limited to the preparation of: crowns, inlays, onlays, full dentures, partial dentures, Maryland Bridges, etc.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process of electroforming a metal to produce a dental prosthesis, the improvement comprising employing as said metal a metallic glass alloy of cobalt and phosphorus containing 8–30% by weight of phosphorus.

2. A process according to claim 1, wherein the phosphorus content is at least 10% by weight.

3. A process according to claim 1, wherein the said metallic glass alloy has a thickness of at least 10 μm.

4. A process according to claim 1, wherein the said metallic glass alloy has a thickness of 100–2000 μm.

5. An electroformed dental prosthesis as produced by the process of claim 1.

6. An aqueous electrolytic bath comprising:

15-300 g/L $CoSO_4.7H_2O$
40-80 g/L $CoCl_2.6H_2O$
25-35 g/L $H_3BO_3$
30-100 g/L $H_3PO_3$
1-2 ml/L wetting agent
pH about 0.8-2.0.

7. An aqueous electrolytic bath according to claim 6, of the following composition:

| | |
|---|---|
| $CoSO_4.7H_2O$ | 200 g/L |
| $CoCl_2.6H_2O$ | 60 g/L |
| $H_3BO_3$ | 30 g/L |
| $H_3PO_3$ | 50 g/L |
| wetting agent | 1 ml/L |
| pH | 1.0. |

8. A process according to claim 1, comprising the steps of:
   (a) producing an impression of a patient's teeth;
   (b) chemically depositing a layer of silver inside said impression;
   (c) coating the resultant die with lacquer in areas where electrodeposition is undesired;
   (d) immersing the die in an electrolyte and passing a current through an electrolyte and the die for a sufficient time to obtain the desired thickness of the cobalt-phosphorus metallic glass alloy; and
   (e) optionally, grinding rough edges of the electroformed prosthesis.

9. A process according to claim 1, wherein an electroformed layer of copper is applied to the die prior to deposition of the cobalt-phosphorus layer, and the copper layer is dissolved in an acid solution after the die is dissolved so as to leave a space for adhesive in the resultant electroformed cobalt-phosphorus metallic glass dental prosthesis.

10. An electroformed product comprising an electroformed dental prosthesis of a cobalt-phosphorus metallic glass alloy containing 8-30% by weight of phosphorus and, on the underside of said dental prosthesis, a removable layer of electroformed copper.

11. A process according to claim 8, wherein the die is dissolved in a solution of methylene chloride and formic acid.

12. A process according to claim 11, wherein the composition of the solvent is 90-95% by weight methylene chloride and 5-10% by weight formic acid.

13. A process according to claim 8, wherein the current is direct current applied between 150-300 $mA/cm^2$.

14. A process according to claim 8, wherein said current is a pulsed galvanostatic current at approximately 300 $mA/cm^2$ with 200 μs on time and 400 μs off time.

15. A process according to claim 8, the electrodeposition being conducted at a temperature of about 40°-85° and the electrolyte having the following compositions:

| | |
|---|---|
| $CoSO_4.7H_2O$ | 200 g/L |
| $CoCl_2.6H_2O$ | 60 g/L |
| $H_3BO_3$ | 30 g/L |
| $H_3PO_3$ | 50 g/L |
| wetting agent | 1 ml/L |
| pH | 1.0. |

* * * * *